United States Patent
Hannemann et al.

(10) Patent No.: US 8,554,921 B2
(45) Date of Patent: Oct. 8, 2013

(54) DEVICE FOR WIRELESS DATA EXCHANGE AS WELL AS METHOD FOR ESTABLISHMENT OF A WIRELESS CONNECTION BETWEEN IN PARTICULAR A MEDICAL SENSOR UNIT AND A COMPUTER

(75) Inventors: Thilo Hannemann, Erlangen (DE); Markus Schild, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1471 days.

(21) Appl. No.: 11/616,359

(22) Filed: Dec. 27, 2006

(65) Prior Publication Data
US 2007/0146130 A1 Jun. 28, 2007

(30) Foreign Application Priority Data
Dec. 27, 2005 (DE) .......................... 10 2005 062 579

(51) Int. Cl.
*G06F 15/16* (2006.01)
*A61B 6/14* (2006.01)

(52) U.S. Cl.
USPC .......... 709/227; 378/91; 378/170; 340/539.22

(58) Field of Classification Search
USPC ...... 378/98.9, 168, 184, 4, 91, 170; 342/463; 250/370.09; 709/227; 340/539.22
See application file for complete search history.

(56) References Cited

U.S. PATENT DOCUMENTS

| | | | |
|---|---|---|---|
| 7,231,258 B2 * | 6/2007 | Moore et al. | 607/60 |
| 2002/0013518 A1 * | 1/2002 | West et al. | 600/300 |
| 2004/0005032 A1 * | 1/2004 | Nanni et al. | 378/168 |
| 2004/0065837 A1 * | 4/2004 | Schick et al. | 250/370.08 |
| 2004/0066898 A1 * | 4/2004 | Schick et al. | 378/98.9 |
| 2005/0211908 A1 * | 9/2005 | Dieras et al. | 250/370.09 |
| 2007/0001905 A1 * | 1/2007 | Eronen | 342/463 |
| 2007/0053498 A1 * | 3/2007 | Mandelkern et al. | 378/184 |
| 2007/0077899 A1 * | 4/2007 | Yang et al. | 455/90.3 |
| 2007/0223649 A1 * | 9/2007 | De Godzinsky | 378/4 |

FOREIGN PATENT DOCUMENTS

DE 10 2005 018 444 11/2005
WO WO 03/021877 A1 3/2003

OTHER PUBLICATIONS

Specification of the Bluetooth System, Nov. 5, 2003, Bluetooth SIG, vol. 8, retrieved from https://www.bluetooth.org/docman/handlers/DownloadDoc.ashx?doc_id=14492 on May 22, 2009.*
D-Link ("High-Speed 2.4 Ghz Wireless Access Point", Jun. 4, 2004, http://web.archive.org/web/20040604234906/http://www.dlink.com/products/?pid=326, pp. 1-13).*

* cited by examiner

*Primary Examiner* — Jungwon Chang
(74) *Attorney, Agent, or Firm* — Schiff Hardin LLP

(57) ABSTRACT

An apparatus and method to enable a simple installation of a sensor unit (in one example an intra-oral x-ray sensor) on a network. The sensor unit is preferably a sensor in the medical field, and it is provided that the sensor unit is itself fashioned as an access point and establishes its own network on which a computer automatically logs on in order to enable a data transfer between the sensor unit and the computer. Due to this measure no expertise is necessary for the installation of the sensor unit.

12 Claims, 1 Drawing Sheet

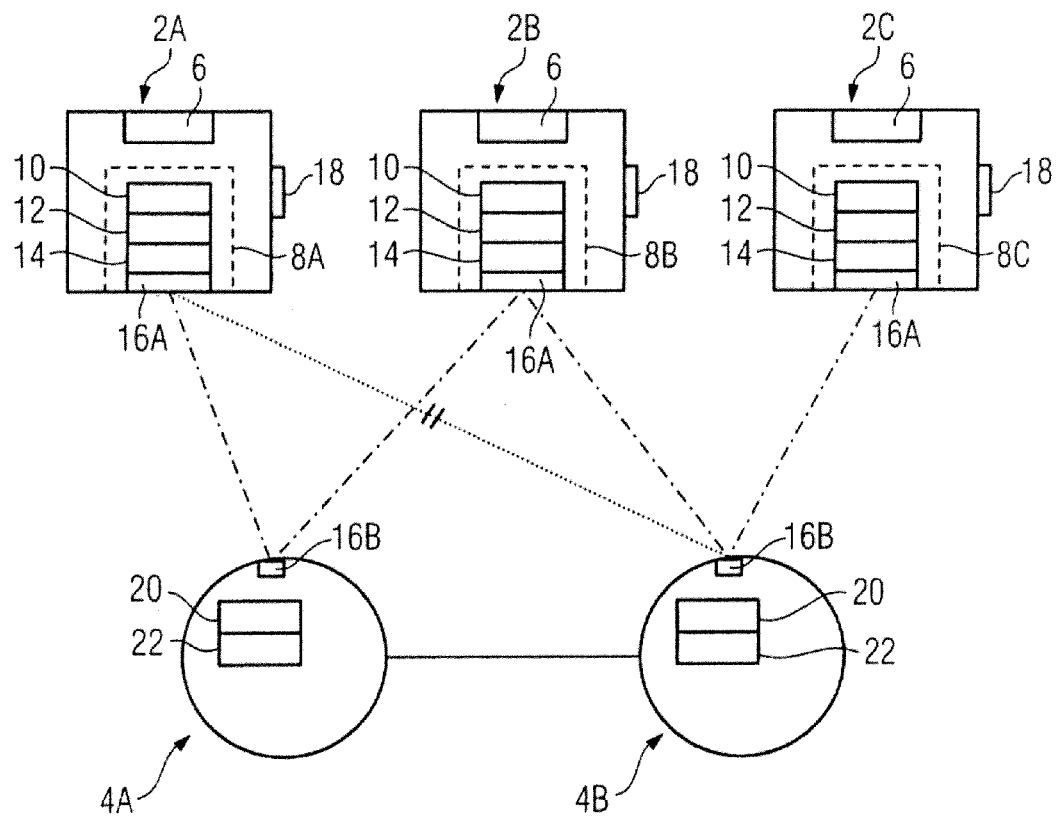

DEVICE FOR WIRELESS DATA EXCHANGE AS WELL AS METHOD FOR ESTABLISHMENT OF A WIRELESS CONNECTION BETWEEN IN PARTICULAR A MEDICAL SENSOR UNIT AND A COMPUTER

BACKGROUND OF THE INVENTION

1. Field of the Invention

The present invention relates generally to a device as well as a method for wireless data exchange between a sensor unit and a computer. In particular, a medical sensor unit is provided as the sensor unit.

2. Description of the Related Art

In the medical field, diagnosis or therapy apparatuses are used that acquire data with the aid of sensors or sensor units, the data subsequently being transmitted to a computer and evaluated there. Such sensor units can include, for example, x-ray detectors that supply digital data that is subsequently evaluated and assembled into image information. For example, in dental medical technology, x-ray sensor units are used that are employed for intra-oral examinations. In order to have an optimally large open space for the examination and in order to avoid the presence of connection cables that may interfere with movement of the medical personnel, modern intra-oral x-ray sensors transfer the data to the computer ensues wirelessly. Any other sensor units (such as, for example, optical camera units) may be provided instead of the x-ray sensor.

With the increasing amount of equipment used in a medical practice or in a clinic, in particular electronic equipment, the need exists to integrate these devices into a uniform computer system in an optimal way in order to not have to keep ready a separate evaluation station (thus a separate computer) for every single sensor unit. In a typical installation, an IT environment (for example a local network) into which the sensor units must be integrated already exists. Without the necessary expertise, however, integration of the sensor into the network is generally not possible without further measures, especially if the network connection is a wireless data exchange. Such expertise in the field of IT technology cannot, however, normally be assumed of medical personnel. Rather than requiring that the medical personnel possess advanced technical skills, the requirement here is to design the IT environment such that integration of such a sensor unit is as simple as possible.

The possibility exists in principle to resort to what is known as WLAN technology (wireless local area network). However, without specific IT knowledge, a simple integration according to the plug-and-play principle is not possible given this technology since the WLAN standard does not support a "plug-and-play installation".

Due to the rapid further development of products for WLAN technology, the use of standard components is necessary in order to also ensure the secure and reliable functionality of the system in the future. This eliminates the possibility of modifying the protocols that form the basis of the WLAN standard in order to enable a "plug-and-play" device.

In a WLAN network, the possibility of establishing what is known as an "ad hoc connection" exists in principle, thus resulting in the formation of what is known as an ad hoc network. However, under the WLAN standard 802.11, connections between a maximum of two apparatuses are generally reliable. An ad hoc network with a plurality of participants offers only a low reliability.

A further approach for the integration of the sensor unit into the network is to integrate the sensor as what is known as a "client" into an existing network in which the computer is also integrated either wirelessly or in a wired manner. What are known as access points are hereby typically provided for the wireless integration of a client. However, the problem exists that the frequency band used for wireless transfer in a WLAN can also be utilized by third parties, such that special measures requiring technical expertise are necessary in order to achieve an insensitivity to interfering external influences, particularly to provide the reliability and security necessary for medical technology. Even with such technical expertise, complete insensitivity to interference is normally not securely assured when, for example, a further access point on the same channel (thus with the same frequency band) is set up in the immediate environment. Furthermore, technical expertise is likewise required for handling of the acquired data and its transmission within the network infrastructure. In particular, the integration requires knowledge about the existing infrastructure, such as the existence of firewalls, the use and allocation of IP addresses, and the like. Without technical expertise, a plug-and-play installation is therefore not possible with the typically-provided concepts.

SUMMARY OF THE INVENTION

The present invention provides a method and apparatus to enable a simple installation of a connection, such as a wireless connection between a sensor and a computer, in particular for the medical field.

The simple connection is achieved via a device for wireless data exchange with a sensor unit for acquisition of data, in particular a medical sensor unit such as, for example, an intra-oral camera or an intra-oral x-ray sensor. The device furthermore comprises a computer for receipt and for processing of the data acquired by the sensor unit. This computer is typically a PC and is subsequently also designated as a "client PC". In principle such a computer can also be a server or another end apparatus. In order to enable a simple installation in the manner of plug-and-play, in this device the sensor unit itself is fashioned as an access point for the establishment of a network connection to the computer.

In contrast to the typical WLAN concepts in which a new apparatus (generally known as a client) is respectively integrated into an existing network, this method takes the reverse path in that the sensor unit itself forms an access point that establishes a network as needed in which the respective computer then logs on. The decisive advantage given this procedure is that the sensor unit is not integrated into an existing network, but rather the sensor unit establishes its own network. The configuration of the sensor unit is thereby possibly independent of the existing network. No knowledge of the network structure of the existing network is thus necessary. At the same time, the sensor unit has control over all necessary parameter settings for the network since it establishes the network itself. Due to the complete independence of the sensor from an existing network, an installation according to the plug-and-play method is therefore enabled without problems.

The necessary technical hardware and software requirements must merely be met in the sensor unit. However, the meeting of these requirements is provided by the manufacturer where the necessary expertise exists. In other words, the expertise for providing the network connection is required only for the sensor manufacturer and is not required of the medical personnel at the user's facility. At the same time, suitable technical program devices are provided on the computer that can likewise be installed without problems, such that overall no expertise is necessary for the installation. If the computer is integrated into an existing network, the data can be transferred wirelessly via the network that is established by the sensor unit into the existing network and this data can be arbitrarily distributed there.

In order to enable a simple installation routine, it is appropriately provided that a network adapter is provided in the computer, the network adapter being configured such that the computer automatically logs onto the network established by the sensor unit. The network adapter is hereby fashioned as a type of driver software or an interface. Existing technologies can hereby be resorted to. As soon as the computer detects that an access point of the network (in the present example, a sensor unit) is present in its proximity, the computer automatically starts a connection to the sensor unit. Thus, no additional routines and installation measures are required here, such that a very user-friendly administration or operation is enabled.

In order to enable an unambiguous identification of the network established by the sensor unit, an unambiguous and predetermined network identifier is associated with this that is preset in the computer. In particular the automatic connection establishment is enabled via the network identifier. This network identifier is typically designated as an SSID (Service Set Identifier) identifier. This is set in the sensor unit in a suitable driver software or, respectively, is set via an installation program that is simple to operate.

BRIEF DESCRIPTION OF THE DRAWINGS

FIG. 1 is a schematic representation showing a simplified representation of an embodiment of the invention, including a device with a plurality of sensor units and a plurality of computers that are wirelessly connected with one another for data exchange.

DETAILED DESCRIPTION OF THE PREFERRED EMBODIMENTS

The present invention, according to a preferred development as shown in FIG. 1, has a sensor unit that includes a DHCP (Dynamic Host Configuration Protocol) module for automatic assignment of an IP (Internet Protocol) address to the computer. The dynamic host configuration protocol, which (in interaction with the a suitable hardware (DHCP server) provided via the DHCP module) implements the dynamic assignment of an IP address (Internet Protocol address) and further configuration parameters to the computer in a network (such as, for example, the Internet or a WLAN (Wireless Local Area Network) or, respectively, LAN (Local Area Network) network). The integration of a new component into an existing network without further configuration is generally possible via DHCP. It is merely required that the automatic acquisition of the IP address is set in the client (which here is the computer). The sensor unit therefore automatically assigns an IP address to the computer via the DHCP module in order to be able to unambiguously address the computer for the data exchange. Given the use of a plurality of computers used in parallel, this is in particular advantageous in order to ensure an unambiguous association. Due to the dynamic IP address assignment this is advantageously, respectively conducted anew upon connection establishment such that the IP addresses are not used up.

According to a preferred development, the sensor unit comprises a further module designated in the following as a RADIUS module. The term RADIUS here stands for remote authentication dial-in user service and is a client-server protocol which serves for authentication and authorization of users given log-in connections in a computer network. The RADIUS module is hereby fashioned as a type of what is known as a RADIUS server which is provided for authentication of the computer with regard to the sensor unit. The authentication hereby in particular serves for establishment of a secure connection (in particular on the basis of a certificate) without the input of a password being necessary. Alternatively, the connection establishment can also ensue on the basis of a user name and password which must be input.

A software module is advantageously installed in particular on the computer, via which software module the computer communicates with the sensor unit given an established connection. This software module therefore forms a driver software via which the data exchange between the two apparatuses ensues given an effected connection establishment.

The device appropriately comprises a plurality of computers as well as a decision module (in particular a decision module integrated into the sensor unit), whereby this is fashioned such that a selection ensues as to which computer the acquired data are transferred. Due to the selected structure via the design of the sensor unit as an access point on a network, in principle the advantageous possibility exists to connect a plurality of computers with the sensor unit. Furthermore, the possibility also exists to connect a plurality of sensor units respectively as separate access points with different computers. However, the requirement can exist that a specific sensor unit exchanges data with only one specific computer. For example, the evaluation program associated with the respective sensor unit is installed on this specific computer. Via the unambiguous association, this prevents the data from being presented to un-authorized third party computers. For the case that a plurality of computers log into the established network, only one computer or only selected computers are therefore permitted to which the communication then actually ensues. Either a heuristic decision routine is therefore stored in the decision module or it is designed such that specific computers are identified via manual input of the user. This manual selection hereby advantageously ensues in the framework of a one-time parameterization during a first installation.

The sensor unit is hereby appropriately fashioned such that the established network connection to those computers that are not selected by the decision module is terminated again. Further login attempts are advantageously prevented. Via this measure a connection establishment is thus respectively allowed to only the selected computers.

According to an appropriate development, an installation routine via which one or more computers are permanently associated with the sensor unit is provided for the association of the selected computers with the sensor unit. The computers are therefore made known to the sensor units. This installation routine advantageously ensues once and is cable-bound, for example via a USB interface. Alternatively it can also ensue wirelessly. During this installation routine a corresponding parameterization is implemented. Via this measure a conflict with the unauthorized computers (for example of third parties in adjacent office rooms) is precluded. The announcement of the selected computer hereby advantageously ensues via the RADIUS module or also via the distinct apparatus address of the selected computer. This address is typically designated as a MAC (Mandatory Access Control) address or also as a LAN address. In this case, one or more MAC addresses are communicated to the sensor unit and information as to which end apparatuses the communication may exclusively ensue is stored.

According to a preferred development, the sensor unit is further fashioned such that the network is reestablished after an effected data transfer to the computer. No continuouslyexisting network is thus established. This serves merely for data transfer. Since the sensor unit is a wired, mobile sensor apparatus which must also be self-sufficient or autarkic with regard to the power supply and is typically operated with batteries, this measure serves to save energy his is in particular of particular advantage given the relatively small wireless, intra-oral sensor units such as, for example, intra-oral x-ray sensors or intra-oral optical cameras.

It is preferably furthermore provided that the sensor unit switches over to a different frequency range (and therewith to a different channel) given an unsatisfactory radio connection quality. A high connection quality is therefore ensured via this measure. At the same time no external intervention by the user is required for this. This is in particular advantageous for a secure and interference-free data transfer given the use of a plurality of apparatuses operating on the same channels.

With reference to the drawing, the device according to FIG. 1 comprises in total three sensor units 2A-2C, for example an intra-oral x-ray sensor 2A, an intra-oral optical camera 2B and a further sensor apparatus 2C. Furthermore, the device comprises in total two computers 4A and 4B. The data acquired by the sensor units 2A-2C are transferred to the computers 4A and 4B and further processed there. The data transfer from the sensor units 2A-2C to the computers 4A and 4B ensues wirelessly as this is represented via the dash-dot lines. The data transfer can hereby ensue bi-directionally. The two computers 4A and 4B are integrated into a wired network (LAN) which is represented by the solid connection line. Further end apparatuses can be installed within this network, such as, for example printers or other, further wired examination and diagnosis apparatuses (here generally designated as sensor units). The sensor units 2A-2C comprise the actual sensor 6, for example the x-ray sensor or the optical camera.

The three sensor units 2A-2C are respectively set up as what are known as access points 8A-8C, for example each of the sensor units 2A-2C is inherently equipped and operable to establish its own local wireless radio network and to implement a wireless communication with the computers 4A and 4B via this network. This technical hardware and software design of the sensor units 2A-2C as access points 8A-8C is represented by the dashed line. What is known as a RADIUS module 10, what is known as a DHCP module 12 and a decision module 14 are integrated within this access point functionality. Furthermore, a communication interface 16A is provided. Furthermore, each of the sensor units 2A-2C comprises an activation switch or button.

The computers 4A and 4B are in particular commercially-available computers that are presently also designated as client PCs. These computers 4A and 4B are configured for a communication with the sensor units 2A-2C fashioned as access points 8A-8C. In particular, a network adapter 20 as well as a specific driver designated as a software module 22 are implemented for this. The network adapter 20 is hereby fashioned in terms of hardware and software such that the respective computer 4A or 4B respectively automatically logs onto the respective network established by the individual sensor units 2A-2C. A communication interface 16B is also provided on the part of the computers 4A and 4B. Both the sensor units 2A-2C and the computers 4A and 4B are equipped with respectively one radio transmitter or, respectively, one radio receiver (not shown) for the wireless radio transfer.

During the operation, thus when an examination is implemented, the respectively used sensor unit 2A-2C is activated (thus switched on) via the activation switch 18. As an access point 8A the activated unit (for example the sensor unit 2A) thereupon establishes its own wireless WLAN network. Due to the network adapter 20 the individual computers 4A and 4B detect this new network and automatically log onto this network. As soon as the access point 8A detects this login by the computers 4A and 4B, with the aid of the decision module 14 it is checked with which of the computers 4A and 4B a data exchange should ensue. The decision hereby in particular ensues on the basis of a previously effected parameterization in which the computer 4A was distinctly assigned to the sensor unit 2A via its MAC address, in particular via a USB (Universal Serial Bus) interface and via a manual selection.

In the exemplary embodiment, the sensor unit 2B is provided in parallel for a data exchange with both computers 4A and 4B. In this case the MAC addresses of both computers 4A and 4B are thus stored in the decision module 14. The sensor unit 2C is in turn associated only with the computer 4B.

As an alternative to the association via the MAC address, this can also ensue via the RADIUS module 10. An authentication and authorization of the respective computer 4A or 4B for the access to the respective network of the individual sensor units 2A-2C is implemented via this RADIUS module. The authorization hereby in particular ensues on a certificate basis without the necessity of the input of a password, i.e. automatically. In particular an encrypted transfer of the data is implemented via the authentication on the basis of a certificate.

After the sensor unit 2A has detected that both computers 4A and 4B have logged onto the network, but that only the computer 4A is authorized for a data exchange, the sensor unit 2A automatically terminates the connection to the computer 4B again (as is indicated by the dotted line to the computer 4B). New login attempts are immediately blocked.

Since the data are transferred from the sensor unit 2B to a plurality of computers 4A and 4B, an unambiguous addressing of the respective computer 4A and 4B is required for the data exchange. For this an IP address is automatically and dynamically (for example, anew after each network establishment) allocated and assigned by the sensor unit 2B to the computers 4A and 4B. The DHCP module 12 is provided and responsible for this.

The data and information acquired via the sensor 6 are transmitted from the sensor unit 2A via the established network connection to the computer 4A. There these are prepared and evaluated. For example, for this a suitably-designed image processing or image manipulation software is installed on the computer 4A. After the transfer of the data (thus after implementation of the examination) the sensor unit 2A automatically switches off and likewise dismantles the network again.

The particular advantage of the embodiment of the sensor units 2A-2C as access points 8A-8C is that no modifications to the sensor units 2A-2C themselves are necessary for installation of these sensor units 2A-2C since these can be (and preferably also are) entirely pre-configured at the factory. In addition to the modules 10 through 14 already described, a special network identifier (SSID) is associated with the respective access point 8A-8C, which network identifier is set in a driver software of the sensor unit 2A-2C. In the event that it is necessary this network identifier can also only be set on site via a suitable installation program in the framework of an installation routine.

Only the computers 4A and 4B must be prepared for the communication with the sensor units 2A-2C. However, no specific knowledge is required for this. Rather, this can ensue in the framework of a simple installation routine, for example with the aid of an installation program supplied together with the respective sensor unit 2A-2C. Since the network respectively established by the individual sensor units 2A-2C is namely independent of the already-existing local network, no data of the existing local network needs to be known. All necessary information that must be communicated to the respective computer 4A and 4B can therefore be comprised in an installation program tuned to the respective sensor unit 2A-2C. Alternatively, for the installation a USB interface on both apparatuses can be drawn upon for a wired communication for installation purposes. The necessary settings and parameters between the sensor unit 2A-2C and the respective computer 4A-4B are exchanged via this wired connection. Manual inputs can hereby be provided by the user. For example, the association of which computer 4A and 4B should be associated with which sensor unit or even the allocation of self-descriptive designations for the individual computers 4A or 4B that are associated with the respective MAC address. The computer 4A or 4B is therefore respectively made known to the sensor unit 2A-2C in this manner via the USB interface.

Via the notification, thus the unambiguous association of the sensor units 2A-2C with the computers 4A and 4B, conflict situations are avoided that, for example, can occur when a plurality of medical practices are arranged in immediate spatial proximity to one another and use the same sensor units 2A-2C.

A further advantage of the embodiment of the sensor units 2A-2C as access points 8A-8C is to be seen in that the computers 4A and 4B are typically arranged in immediate spatial proximity to the sensor units 2A-2C, in particular in the same examination room. This spatial proximity is advantageous for a good data transfer, in conventional WLAN networks this is typically not the case since here the wireless connection often ensues across a plurality of rooms since, for example, an access point used for the wireless transfer (and onto whose network the sensor unit would have to log on as a client) is located in an adjacent room. This has the consequence that the sensor unit would have to initially log onto the network of the remote access point and the data transfer would again ensues to the computer arranged at close range.

In order to optimally stop interferences, it is furthermore provided that the sensor units 2A-2C are fashioned such that they automatically shift to another channel (thus to a different radio frequency) given a poor transfer quality. Since the sensor units 2A-2C here establish the radio network themselves via their access points 8A-8C, this is possible without problems.

Thus, there is shown and described a device that enables a simple installation of a sensor unit (in one example an intra-oral x-ray sensor), in particular in the medical field, and it is provided that the sensor unit is itself fashioned as an access point and establishes its own network on which a computer automatically logs on in order to enable a data transfer between the sensor unit and the computer. Due to this measure no expertise is necessary for the installation of the sensor unit.

Although other modifications and changes may be suggested by those skilled in the art, it is the intention of the inventors to embody within the patent warranted hereon all changes and modifications as reasonably and properly come within the scope of their contribution to the art.

We claim:

1. An apparatus for wireless data exchange, comprising:
   a wireless intra-oral sensor unit including a medical image sensor operable to obtain intra-oral image data of a patient, said sensor unit including a wireless communication device connected to said medical image sensor; and
   a computer system including a wireless communication device through which the computer system communicates with said wireless communication device of said sensor unit for receipt of the intra-oral image data acquired by said sensor unit;
   said wireless intra-oral sensor unit comprising a module for establishing a wireless network via the wireless communication device of the sensor unit and defining an access point of a wireless network for connection to said medical image sensor, said wireless network being wirelessly sensed by the computer system and to which the computer system connects; said sensor unit comprising an IP address module that automatically allocates an IP address to said computer system;
   wherein said computer system includes a plurality of computers each with a wireless communication device, said sensor unit includes a decision module that selects one of said plurality of computers for receiving the image data acquired by the sensor unit.

2. An apparatus according to claim 1, wherein said computer system includes a module that senses the access point of said sensor unit and automatically logs onto a network established by said sensor unit.

3. An apparatus according to claim 2, wherein said wireless communication devices of said sensor unit and said computer system assign a predetermined network identifier to the network established by the sensor unit, and said network identifier being preset in said computer system.

4. An apparatus according to claim 1, wherein said sensor unit comprises a module that authenticates said computer system to said network.

5. An apparatus according to claim 1, further comprising:
   a software module operating on said computer system to enable said computer system to communicate with said sensor unit given an established connection.

6. An apparatus according to claim 1, wherein said decision module of said sensor unit terminates network connections to non-selected computers.

7. An apparatus according to claim 1, wherein said wireless communication module of said sensor unit is programmed to be permanently associated with said computer system via an installation routine, such that a wireless connection is established by the sensor unit only with said computer system.

8. An apparatus according to claim 1, wherein said wireless communication module of said sensor unit disconnects the network connection with said computer system after effecting a data transfer of medical image data obtained by said sensor to said computer system.

9. An apparatus according to claim 1, wherein said wireless communication module of said sensor unit establishes a wireless network at a first frequency range with said computer system and wherein said wireless communication module of said sensor unit switches to a different frequency range given an unsatisfactory radio connection quality on the wireless network at said first frequency range.

10. An apparatus according to claim 1, further comprising: a plurality of further sensor units including wireless communication devices to operate as a respective plurality of access points.

11. An apparatus according to claim 1, wherein said sensor unit is an x-ray sensor.

12. An apparatus as claimed in claim 1, wherein said sensor is an intra-oral x-ray sensor for dental medicine.

* * * * *